(12) United States Patent
Liu

(10) Patent No.: US 12,397,078 B2
(45) Date of Patent: Aug. 26, 2025

(54) AROMATHERAPY MACHINE

(71) Applicant: Dongguan Yiting Household Products Co., Ltd., Dongguan (CN)

(72) Inventor: ShiBo Liu, Dongguan (CN)

(73) Assignee: Dongguan Yiting Household Products Co., Ltd., Dongguan (CN)

( * ) Notice: Subject to any disclaimer, the term of this patent is extended or adjusted under 35 U.S.C. 154(b) by 498 days.

(21) Appl. No.: 17/982,557

(22) Filed: Nov. 8, 2022

(65) Prior Publication Data

US 2024/0108776 A1 Apr. 4, 2024

(30) Foreign Application Priority Data

Sep. 30, 2022 (CN) .......................... 202222634733.3

(51) Int. Cl.
*A61L 9/14* (2006.01)
(52) U.S. Cl.
CPC ........... *A61L 9/14* (2013.01); *A61L 2209/133* (2013.01); *A61L 2209/134* (2013.01)
(58) Field of Classification Search
CPC ....................................................... A61L 9/14
See application file for complete search history.

(56) References Cited

U.S. PATENT DOCUMENTS

| 2020/0368383 A1 | 11/2020 | Feng et al. |
| 2021/0178306 A1 | 6/2021 | Lee |
| 2021/0180827 A1 | 6/2021 | Lee |

FOREIGN PATENT DOCUMENTS

CN 112843315 A * 5/2021 ............... A61L 9/14

OTHER PUBLICATIONS

CN 112843315 English Translation (Year: 2021).*

* cited by examiner

*Primary Examiner* — Sean E Conley

(57) ABSTRACT

An aromatherapy machine includes an atomizing assembly and an essential oil bottle, the atomizing assembly includes a shell, an atomizer and a pump; the essential oil bottle is detachably connected with the lower part of the shell, the pump is provided with a first liquid pipe and a second liquid pipe, which communicated with each other; the shell is provided with a first, pipe, one end thereof enters the essential oil bottle, the other end thereof communicates with the first liquid pipe, an upper part of the shell is provided with a reservoir, a side wall of the reservoir is provided with a second pipe, communicated with the second liquid pipe; the atomizer is arranged above the reservoir. When the aromatherapy machine is used, the pump sucks the essential oil in the essential oil bottle via the first liquid pipe and the first pipe, and conveys the essential oil to the reservoir via the second liquid pipe and the second pipe, and then the essential oil is atomized by the atomizer and is dispelled from the shell.

10 Claims, 4 Drawing Sheets

AROMATHERAPY MACHINE

FIELD OF THE INVENTION

The present invention relates to aromatherapy technical field, more particularly, to an, aromatherapy machine.

BACKGROUND OF THE INVENTION

Incense is a long-lasting technique, and users light incense sticks or flower and grass powder to achieve the effects of dispelling unpleasant smell in the environment, repelling mosquitoes, calming down and concentrating. At present, a common aromatherapy machine performs high-frequency ultrasonic oscillation by means of an atomizing device, atomizes and disperses the essential oil extracted from plant into the air, which has a small volume, is convenient to use, and is applied in various living and working scenarios.

The aromatherapy machine in the prior art has complex structure and is difficult to assemble. For example, Chinese Utility Model Patent No.: CN205411747U discloses an aromatherapy machine easy to replace the essential oil container, which includes an air outlet connector, an upper atomizing assembly, a lower atomizing assembly, a connector, an air inlet pipe, an essential oil container, and a base and a spring, all arranged in the shell of the aromatherapy machine. The air outlet connector is embedded in the upper atomizing assembly, and the upper atomizing assembly is provided with an air inlet passing through the lower atomizing assembly to be connected to the connector, one end of the air inlet pipe is connected to the connector, and the other end thereof extends into the essential oil container; a bottom of the essential oil container is provided with the base and the ring for driving the base. In using, the connector, the base and the spring tightly press the essential oil container. The aromatherapy machine also has a rotary mechanism facilitating opening when replacing the essential oil container.

In the aromatherapy machine, air reaches the connector from the air inlet through the lower atomizing assembly, and then enters the essential oil container through the air inlet pipe. During this process, the air flows slowly and has a relatively large loss, so that the amount of essential oil atomized by an atomizer each time is relatively little, the amount of mist produced is relatively little, which can not satisfy the requirements of a user, and the structure of the aromatherapy machine is complex. Therefore, it is necessary to improve the prior art to solve the above problems.

SUMMARY OF THE INVENTION

The object of the present invention is to provide an aromatherapy machine to solve the problems that the aromatherapy machines in the prior art produce mist with relatively litter amount and have complex structures.

In order to achieve the above object, the present invention provides an aromatherapy machine, which includes an atomizing assembly and an essential oil bottle, the atomizing assembly includes a shell, an atomizer and a pump; the essential oil bottle is detachably connected with the lower part of the shell, the pump is provided with a first liquid pipe and a second liquid pipe, which communicated with each other; the shell is provided with a first pipe, one end thereof enters the essential oil bottle, the other end thereof communicates with the first liquid pipe, an upper part of the shell is provided with a reservoir, a side wall of the reservoir is provided with a second pipe, communicated with the second liquid pipe; the atomizer is arranged above the reservoir.

According to one embodiment in the present invention, the inner wall of the shell extends a baffle plate, a centre of the baffle plate is provided with a plug-in port downwards, the plug-in port is inserted into an opening of the essential oil bottle, and the first pipe passes through the plug-in port to reach the bottom of the essential oil bottle.

According to one embodiment in the present invention, a first flowing chamber is provided between the reservoir and the inner wall of the shell, the first flowing chamber is above the plug-in port, the liquid gathered at the bottom of the atomizer passes through the first flowing chamber and the plug-in port to flow back to the essential oil bottle.

According to one embodiment in the present invention, the shell is below the baffle plate, the inner wall of the shell is provided with an internal thread, the opening of the essential oil bottle is provided with an external thread, the shell and the essential oil bottle are detachable connected by the internal thread and the external thread.

According to one embodiment in the present invention, the aromatherapy machine also has a guiding piece arranged on the upper part of the shell and above the atomizer.

According to one embodiment in the present invention, the guiding piece has a cover and a funnel-shaped opening provided on the cover, the cover covers a top of the shell, and the water mist from the atomizer flows out of the funnel-shaped opening.

According to one embodiment in the present invention, the cover extends to form two lugs; the lugs are attached to an outer wall of the shell; and the lugs and the outer wall of the shell are respectively provided with a clamping protrusion and a clamping groove which cooperate with each other.

According to, one embodiment in the present invention, the aromatherapy machine also has a housing, the atomizing assembly is loaded on the housing.

According to one embodiment in the present invention, the first pipe reaches the bottom of the essential oil bottle, and the opening of the first pipe is obliquely arranged relative to a cross section thereof.

According to one embodiment in the present invention, the housing is annular shell, the essential oil bottle is loaded on an inner ring of the annular shell, a lamp strip is provided on the inner ring of the annular shell, and the lamp strip irradiates the essential oil bottle.

According to one embodiment in the present invention, the aromatherapy machine also has a power supply assembly, which is mounted in the housing to power the pump. The housing is provided with a printed circuit board and a power interface, and the printed circuit board is electrically connected to the pump.

one or more of the technical schemes provided according to the embodiment in the present invention have at least one of the following technical effects:

When the aromatherapy machine is used, the pump sucks the essential oil in the essential oil bottle via the first liquid pipe and the first pipe, and deliveries the essential oil to the reservoir via the second liquid pipe and the second pipe, and then the essential oil is atomized by the atomizer and is dispelled from the shell. The aromatherapy machine can transport a sufficient amount of essential oil to the atomizer, and has a large atomizing amount. Moreover, the structure of the aromatherapy machine is fine, simple, and easy to manufacture and assemble.

BRIEF DESCRIPTION OF THE DRAWINGS

In order to explain more clearly the technical scheme in the embodiment of the present invention, a brief introduction is given below to, the attached drawings needed in the embodiment. Obviously, the attached drawings in the following description are only some embodiments of the present invention, for ordinary technicians in this field, other drawings can be obtained according to these drawings without paying creative labor.

DETAILED DESCRIPTION OF ILLUSTRATED EMBODIMENTS

Figure 1:
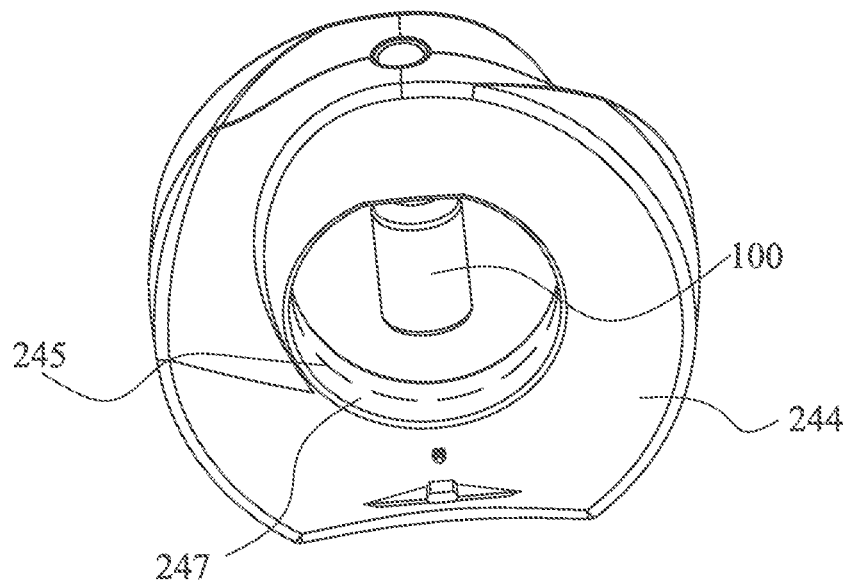
FIG. 1 is a structural diagram of the aromatherapy machine according to the embodiment in the present invention.

The embodiment of the present invention is described in detail below, and an example of the embodiment is shown in the attached FIGS., where the same or similar label from beginning to end represents the same or similar element or element with the same or similar function. The following embodiments described by reference to the attached drawings are exemplary and are intended to be used to explain the embodiments of the present invention, and can not be understood as limiting the present invention.

In the description of the embodiment of the present invention, it needs to be understood that the azimuth or position relation indicated in the term "length", "width", "upper", "lower", "front", "rear", "left", "right", "vertical", "horizontal", "top", "bottom", "inside", "outside" and so on is based on the azimuth or position relation shown in the attached figure, only for the convenience of describing the embodiment and simplifying the description of the present invention, rather than indicating or implying that the device or element must have a specific orientation, construction and operation with a specific orientation, so it can not be understood as a restriction on the present invention.

Furthermore, the terms "first", "second" are used only for descriptive purposes and can not be understood as indicating or implying relative importance or implicitly indicating the number of technical features indicated. Thus, the qualification of "first" and "second" features may include one or more of them explicitly or implicitly. In the description of the embodiment of the present invention, the meaning of "multiple" is two or more, unless otherwise specified.

In the embodiments of the invention, unless otherwise clearly specified and defined, the terms, "installed", "connected", "or" fixed "should be generally understood, for example, a fixed connection, or a removable connection, a mechanical connection or an electrical connection, or an directly connection or an indirectly connection through an intermediate media, or a connection within two elements or the interaction of two elements. For those of ordinary skilled in the art, the specific meaning of the above terms in the embodiment of the present invention may be understood under specific circumstances.

Referring to FIG. 1-FIG. 6, an aromatherapy machine includes an atomizing assembly 200 and an essential oil bottle 100. The atomizing assembly 200 includes a shell 210, an atomizer 220 and a pump 230. The essential oil bottle 100 is detachably connected with a lower part of the shell 200, the pump 230 is provided with a first liquid pipe 231 and a second liquid pipe 232 communicated with each other; the shell 210 is provided with a first pipe 211, one end of the first pipe 211 enters the essential oil bottle 100, the other end thereof is communicated with the first liquid pipe 231, an upper part of the shell 210 is provided with a reservoir 213, a side wall of the reservoir 213 is provided with a second pipe 212 communicated with the second liquid pipe 232; the atomizer 220 is arranged above the reservoir 213. When the aromatherapy machine is used, the pump 230 sucks the essential oil in the essential oil bottle 100 via the first liquid pipe 231 and the first pipe 211, and deliveries the essential oil to the reservoir 213 via the second liquid pipe 232 and the second pipe 212, and then the essential oil is atomized by the atomizer 220 and is dispelled from the shell 210. The aromatherapy machine can transport a sufficient amount of essential oil to the atomizer 220, and has a large atomizing amount. Moreover, the structure of the aromatherapy machine is fine, simple, and easy to manufacture and assemble.

According to one embodiment in the present invention, an inner wall of the shell 210 extends a baffle plate 214, a centre of the baffle plate 214 is provided with a plug-in port 215 downwards, the plug-in port 215 is inserted into an opening 101 of the essential oil bottle 100, and the first pipe 211 passes through the plug-in port 215 to reach a bottom 102 of the essential oil bottle 100.

Figure 4:
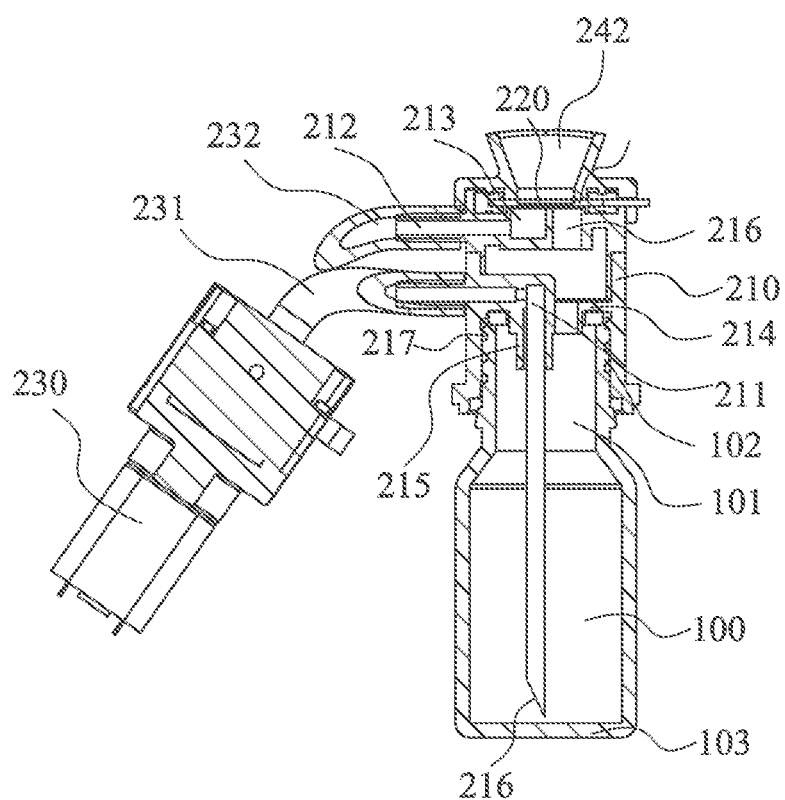
FIG. 4 is a section view along the A-A line in FIG. 3.
Figure 6:
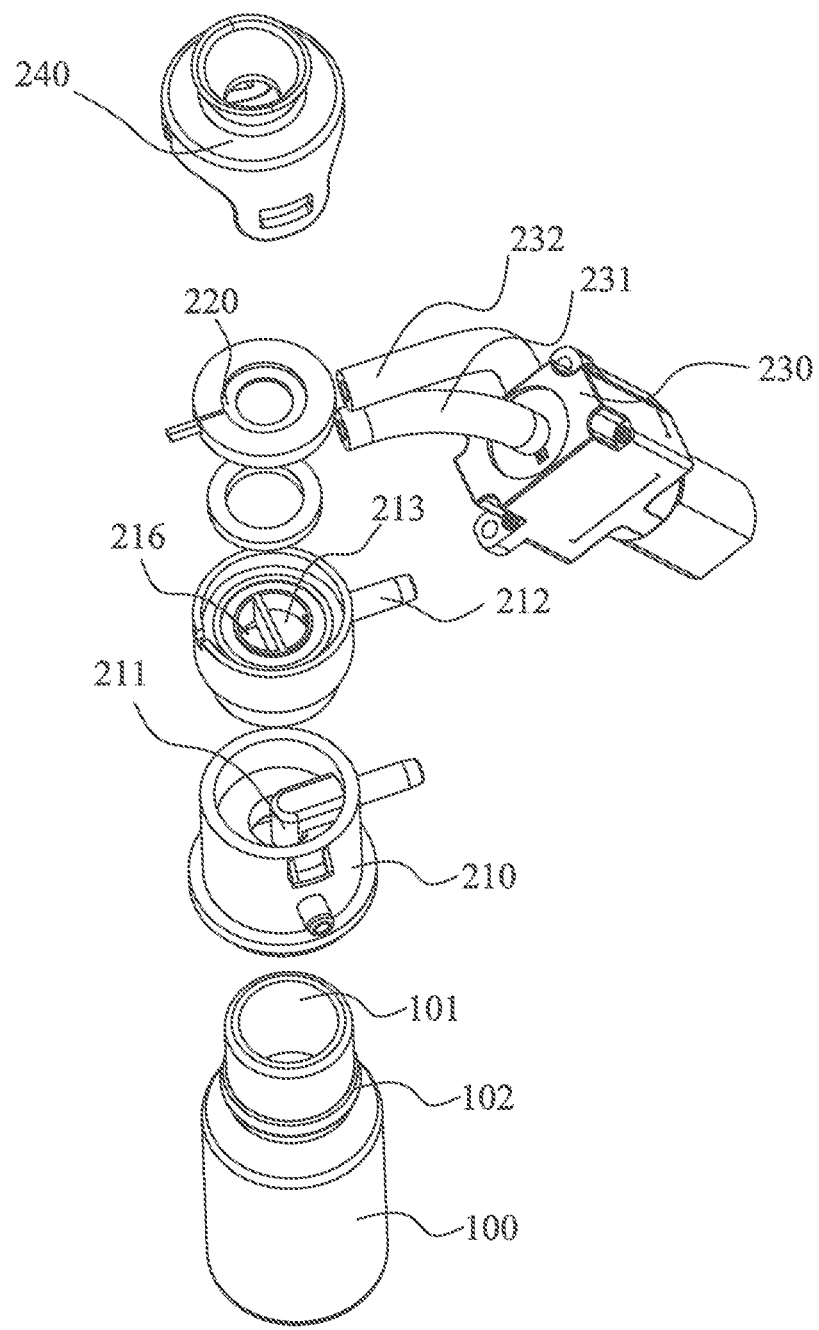
FIG. 6 is decomposition view of FIG. 2.

According to one embodiment in the present invention, referring to FIG. 4 and FIG. 6, a flowing chamber 216 is provided between the reservoir 213 and the inner wall of the shell 210, the flowing chamber 216 is above the plug-in port 215, the liquid gathered at the bottom of the atomizer 220 passes through the flowing chamber 216 and the plug-in port 215 to flow back to the essential oil bottle 100.

According to one embodiment in the present invention, referring to FIG. 4 and FIG. 6, the shell 210 is below the baffle plate 214, the inner wall of the shell 210 is provided with an internal thread 211, the opening 101 of the essential oil bottle 100 is provided with an external thread 102, the shell 210 and the essential oil bottle 100 are detachable connected by the internal thread 211 and the external thread 102, thereby fascinating mounting and disassembly the essential oil bottle.

Figure 2:
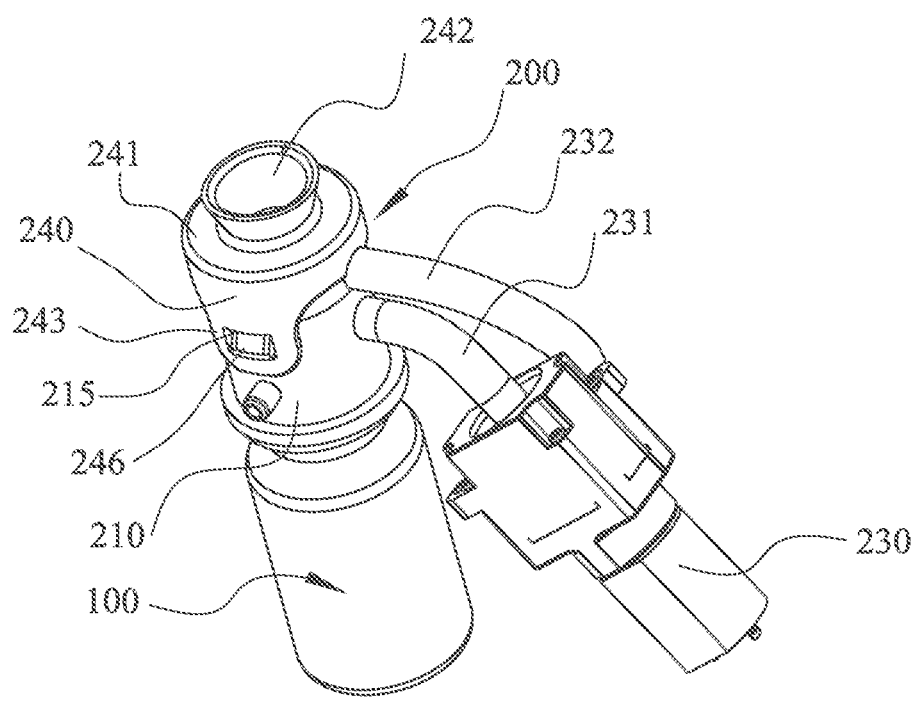
FIG. 2 is the structural diagram of the aromatherapy machine shown in FIG. 1. after removing the housings.
Figure 3:
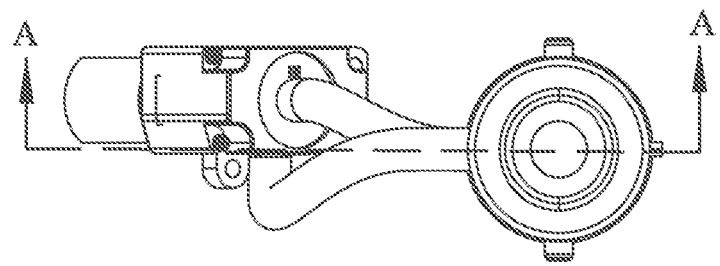
FIG. 3 is a top view of FIG. 2.

According to one embodiment in the present invention, referring to FIG. 2, the aromatherapy machine also has a guiding piece 240 arranged on the upper part of the shell 210 and above the atomizer 220. The guiding piece 240 is used for guiding the water mist formed by the atomization of the essential oil, so that it is ejected according to a certain shape.

According to one embodiment in the present invention, the guiding piece 240 has a cover 241 and a funnel-shaped opening 242 provided on the cover 241, the cover 241 covers a top of the shell 210, and the water mist from the atomizer 220 flows out of the funnel-shaped opening 242. The funnel-shaped opening 242 facilitates the atomization of the essential oil to be gathered firstly and then dissipated, giving a visual aesthetic feeling to a person.

According to one embodiment in the present invention, the cover 241 extends to form two lugs 243; the lugs 243 are attached to an outer wall of the shell 210; and the lugs 243 and the outer wall of the shell 210 are respectively provided with a clamping protrusion 246 and a clamping groove 215 cooperating with each other, thereby fascinating mounting and disassembly the cover 241.

According to one embodiment in the present invention, the first pipe 211 reaches the bottom 103 of the essential oil bottle 100, and the opening 216 of the first pipe 211 is obliquely arranged relative to a cross section thereof, this structure can avoid the opening 216 of the first pipe 211 being blockage and facilitates the suck of the essential oil.

According to one embodiment in the present invention, the aromatherapy machine also has a housing 244, the atomizing assembly 200 is loaded on the housing 244. The housing 244 can be designed as a flower shape, cylinder shape or any other shapes according to the requirement of the user, which has decorative effect. The housing 244 is annular shell, the essential oil bottle 200 is loaded on an inner ring 247 of the annular shell. A lamp strip 245 is provided on the inner ring of the annular shell, and the lamp strip 245 illuminates the essential oil bottle 100 to give it a visual aesthetic.

According to one embodiment in the present invention, the aromatherapy machine also has a power supply assembly, which is mounted in the housing 244 to power the pump.

Figure 5:
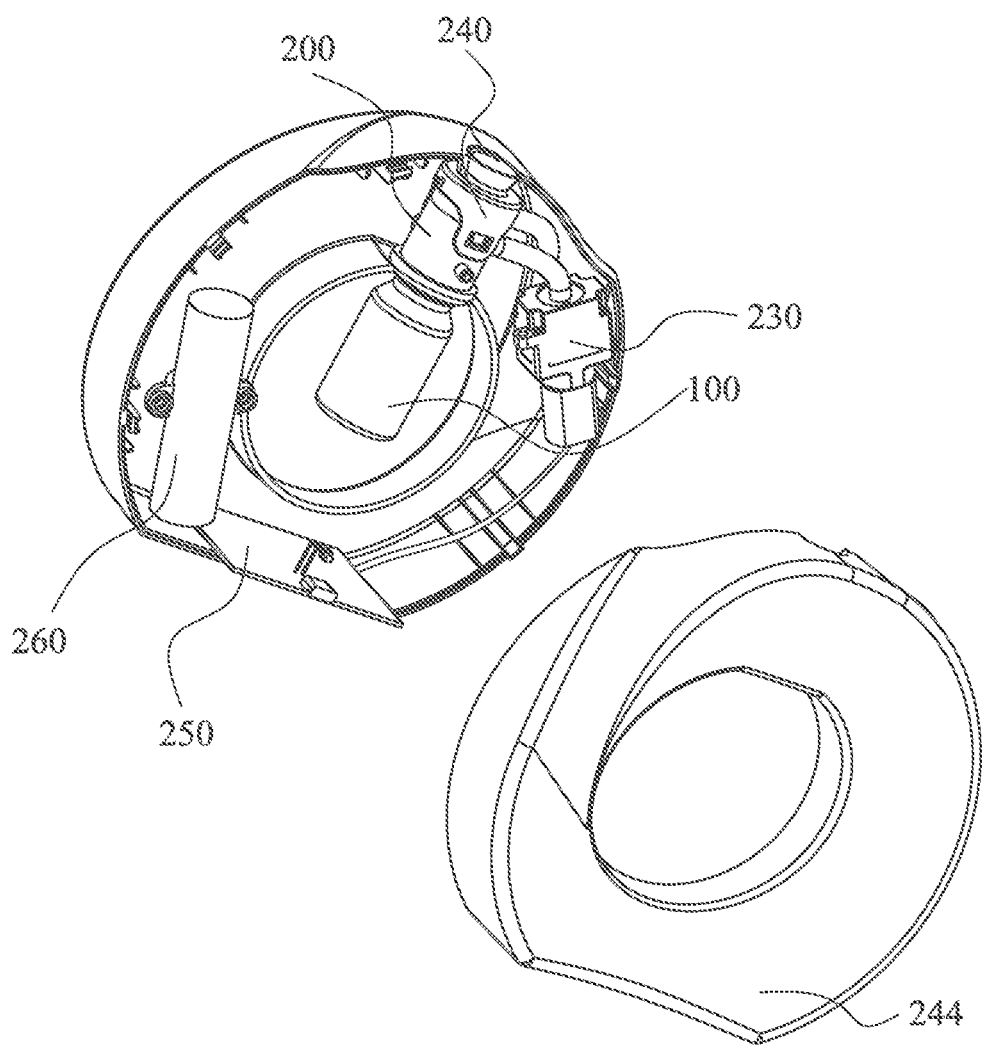
FIG. 5 is a decomposition view of the aromatherapy machine shown in FIG. 1.

According to one embodiment in the present invention, referring to FIG. 5, the housing 244 is provided with a printed circuit board 250 and a power interface 260, and the printed circuit board is electrically connected to the pump 230, thereby power supply the pump 230 through an external power supply.

According to one embodiment in the present invention, the housing 244 is provided with a battery 260, which is electrically connected to the pump 230.

The foregoing descriptions are merely exemplary embodiments of the present invention, but are not, intended to limit the present invention. Any modification, equivalent replacement, and, improvement made within the spirit and principle of the present invention shall belong to the scope of protection of the present utility model.

What is claimed is:

1. An aromatherapy machine, comprising an atomizing assembly and an essential oil bottle, said atomizing assembly includes a shell, an atomizer and a pump; said essential oil bottle is detachably connected with a lower part of said shell, said pump is provided with a first liquid pipe and a second liquid pipe communicated with each other; said shell is provided with a first pipe, one end of said first pipe enters said essential oil bottle, the other end thereof is communicated with said first liquid pipe, an upper part of said shell is provided with a reservoir, a side wall of said reservoir is provided with a second pipe communicated with the second liquid pipe; said atomizer is arranged above said reservoir.

2. The aromatherapy machine according to claim 1, wherein an inner wall of said shell is provided with a baffle plate, a centre of said baffle plate is provided with a plug-in port downwards, said plug-in port is inserted into an opening of said essential oil bottle, and said first pipe passes through said plug-in port to reach a bottom of said essential oil bottle.

3. The aromatherapy machine according to claim 1, wherein a flowing chamber is provided between said reservoir and an inner wall of the shell, said flowing chamber is above said plug-in port, liquid gathered at a bottom of said atomizer passes through said flowing chamber and said plug-in port to flow back to said essential oil bottle.

4. The aromatherapy machine according to claim 2, wherein said shell is below said baffle plate, said inner wall of the shell is provided with an internal thread, said opening of said essential oil bottle is provided with an external thread, said shell and said essential oil bottle are detachable connected by said internal thread and said external thread.

5. The aromatherapy machine according to claim 1, wherein also comprising a guiding piece arranged on an upper part of said shell and above said atomizer.

6. The aromatherapy machine according to claim 5, wherein said guiding piece has a cover and a funnel-shaped opening provided on said cover, said cover covers a top of said shell, and water mist from said atomizer flows out of said funnel-shaped opening.

7. The aromatherapy machine according to claim 6, wherein said cover extends to form two lugs; said lugs are attached to an outer wall of said shell; and said lugs and said outer wall of the shell are respectively provided with a clamping protrusion and a clamping groove cooperated, with each other.

8. The aromatherapy machine according to claim 1, wherein said first pipe reaches a bottom of said essential oil bottle, and an opening of said first pipe is obliquely arranged relative to a cross section thereof.

9. The aromatherapy machine according to claim 1, wherein also comprising a housing, said atomizing assembly is loaded on said housing; said housing is annular shell, said essential oil bottle is loaded on an inner ring of said annular shell, a lamp strip is provided on said inner ring, and said lamp strip irradiates said essential oil bottle.

10. The aromatherapy machine according to claim 8, wherein also comprising a power supply assembly, mounted in said housing to power said pump; said housing is provided with a printed circuit board and a power interface, and said printed circuit board is electrically connected to said pump; said power supply assembly includes batteries.

* * * * *